(12) United States Patent
Dykes

(10) Patent No.: US 6,273,894 B1
(45) Date of Patent: Aug. 14, 2001

(54) VACUUM CANNULA APPARATUS AND METHOD FOR POSITIONING AN INTRAOCULAR LENS IN THE EYE

(75) Inventor: Ronald E. Dykes, The Woodlands, TX (US)

(73) Assignee: STAAR Surgical Company, Inc., Monrovia, CA (US)

( * ) Notice: Subject to any disclaimer, the term of this patent is extended or adjusted under 35 U.S.C. 154(b) by 0 days.

(21) Appl. No.: 09/358,434

(22) Filed: Jul. 22, 1999

(51) Int. Cl.⁷ .................................................... A61F 9/00
(52) U.S. Cl. ................................................................ 606/107
(58) Field of Search ................................................ 606/107

(56) References Cited

U.S. PATENT DOCUMENTS

| | | | |
|---|---|---|---|
| 2,224,575 | * 12/1940 | Montalvo-Guenard | 606/107 |
| 3,994,297 | * 11/1976 | Kopf | 606/107 |
| 4,047,532 | * 9/1977 | Phillips et al. | 606/107 |
| 5,217,465 | * 6/1993 | Steppe | 606/107 |
| 5,364,405 | * 11/1994 | Zaleski | 606/107 |
| 5,733,256 | * 3/1998 | Costin | 606/107 |

* cited by examiner

*Primary Examiner*—Paul J. Hirsch
(74) *Attorney, Agent, or Firm*—Law Offices of Willliam L. Klima, P.C.

(57) ABSTRACT

An apparatus and method for releasably positively gripping and manipulating an implant within the eye. A preferred embodiment includes a vacuum cannula apparatus.

10 Claims, 5 Drawing Sheets

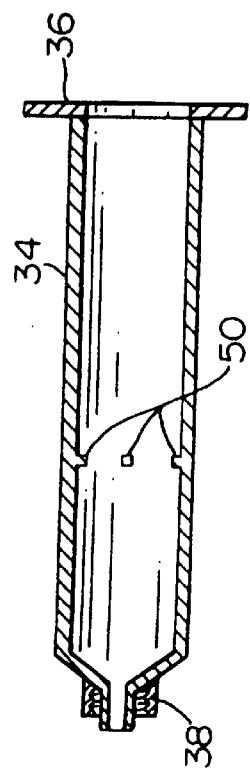
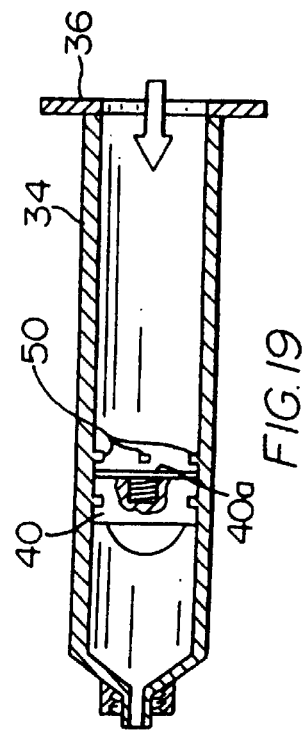
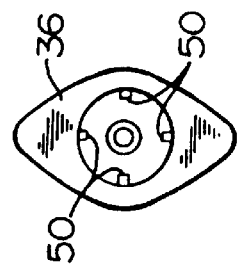
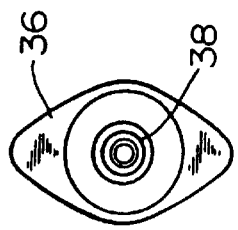
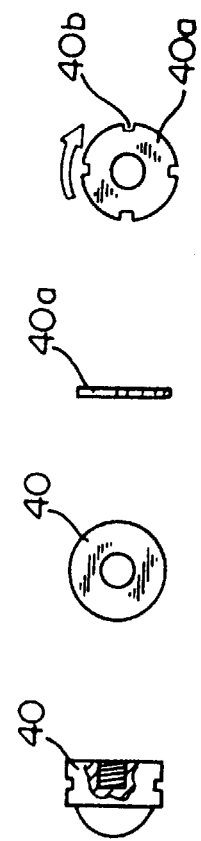
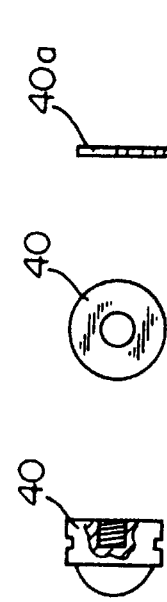
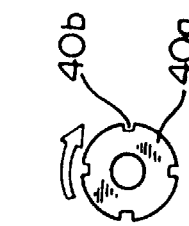
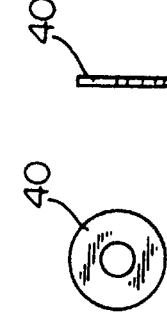

VACUUM CANNULA APPARATUS AND METHOD FOR POSITIONING AN INTRAOCULAR LENS IN THE EYE

FIELD OF THE INVENTION

The present invention is directed to an apparatus and method for positioning an eye implant, in particular, an intraocular lens such as a phakic refractive lens in the eye. The apparatus and method are particularly suitable for use with small incision cataract and/or refractive eye surgery.

BACKGROUND OF THE INVENTION

The conventional method of implanting an intraocular lens in the eye is to provide a small incision of approximately 1.8 millimeters to 2.5 millimeters with either a diamond knife or surgical steel knife in the cornea of the eye. A deformable intraocular lens of the type innovated by STAAR Surgical Company, Inc. of Monrovia, Calif. is folded with either a lens insertion apparatus and/or forceps, and then passed through the small incision in the eye where the lens then unfolds to its operational dimensions. The lens is then manipulated with various surgical instruments such as a small hook type manipulator to move the lens around within the eye into position.

The conventional foldable intraocular lens (IOL) is utilized when the natural crystalline lens is removed by a surgical procedure (i.e. typically by phacoemulsification). Another type of intraocular lens (IOL) referred to as a phakic refractive lens (PRL) for use in the refractive correction of a natural lens can be inserted with the natural crystalline lens left intact, and can then be manipulated with the apparatus and method according to the present invention. STAAR Surgical AG of Switzerland is the innovator of the phakic refractive lens (PRL) and is the manufacturer of the Implantable Contact Lens™ (ICL™). These and other types of implants including anterior chamber type IOLs, posterior chamber type IOLS, intra corneal rings, glaucoma wicks and other implants for use in the eye can be manipulated by the apparatus and method according to the present invention.

In the conventional intraocular surgery, once the intraocular lens is inserted into the eye, the intraocular lens is manipulated by various types of mechanical manipulators which the surgeon uses to push or pull on various portions of the intraocular lens. Typically, there is no direct connection made between the manipulating device and the implant to "positively grip" and move the implant around within the eye by the surgeon. Thus, there is some lack of control in the movement and positioning of the lens within the eye by the surgeon. For example with an IOL, the surgeon typically pushes on an edge portion of the lens or grips an edge of the lens or a hole extending therethrough for pulling on the lens when manipulating the IOL within the eye.

Regarding an IOL for cataract type surgery, it would be an improvement to be able to positively grip a portion of the IOL and quickly and accurately manipulate the lens into position in the proper orientation in a positive manner. A new type of cataract IOL innovated and now sold by STAAR Surgical Company, Inc. of Monrovia, Calif. is a Toric IOL which requires proper orientation in the capsular bag to be effective according to the prescription of the patient. It would be quite helpful to a surgeon to have a manipulating device that positively grips a portion of this type of IOL to properly orientate the lens in the eye.

Regarding eye surgery with a phakic refractive lens (PRL), the phakic refractive lens is inserted through the small incision in a folded or compressed state, and then opens into its operational configuration. The iris is dilated ahead of time to help facilitate placement of the lens between the natural lens and the back of the iris. A surgeon must be particularly careful in manipulating the lens so as not to touch the natural crystalline lens, which could cause a surgically induced cataract. Further, even touching the lens portion of a phakic refractive lens with a manipulating tool could create a surgically induced cataract, since the phakic refractive lens is so thin that a point force can easily penetrate through the lens material. Thus, a surgeon has to be particularly careful in the manipulation of a phakic refractive lens to prevent damage to the natural crystalline lens. In addition, the Implantable Contact Lens manufactured by STAAR Surgical AG is designed with four footpads (i.e. rounder corner protrusions) at the four corners of the lens. During surgery, each footpad needs to be tucked through the opening in the iris to fit between the iris and natural crystalline lens. A surgeon must be particularly careful again, not to cause a surgically induced cataract when tucking each of the four footpads under the iris.

SUMMARY OF THE INVENTION

An object of the present invention is to provide an improved apparatus and method for manipulating an eye implant such as an intraocular lens within the eye.

A second object of the present invention is to provide an improved apparatus and method for manipulating an intraocular lens within the eye so that the intraocular lens is positively gripped when being manipulated.

A third object of the present invention is to provide an apparatus and method for manipulating an intraocular lens within the eye so that the intraocular lens is positively gripped by a fluid vacuum force.

A fourth object of the present invention is to provide an apparatus and method involving the use of a fluid vacuum cannula to positively grip a portion of an intraocular lens for manipulating the lens within the eye.

A fifth object of the present invention is to provide an apparatus and method for manipulating a phakic refractive lens type of intraocular lens within the eye.

The present invention is directed to an apparatus and method for manipulating an intraocular lens within the eye. The intraocular lens can be a cataract type of intraocular lens or a refractive type of intraocular lens. Specifically, the intraocular lens can be of a type to replace the natural crystalline lens in a cataract surgery, or can be of a type to refractively correct the natural crystalline lens. The intraocular lenses are preferably posterior type intraocular lenses, however, the apparatus and method according to the present invention can also be used with anterior chamber type intraocular type lenses. In addition, the apparatus and method according to the present invention can be utilized for manipulating other types of implants such as intra corneal rings, glaucoma wicks, sclera implants, capsular rings, capsular spare parts and other implants to be implanted within the eye of a human or animal.

The apparatus and method according to the present invention positively grips at least a portion of the lens while the lens is being manipulated. Thus, a surgeon can positively manipulate the lens without extraneous or uncontrolled movement thereof when the lens is being positioned within the eye. The term "positively grip" means that there exists a substantial connection between the surgical device and intraocular lens that prevents little or no movement between the surgical device and lens during manipulation of the lens within the eye. Preferably, there exists absolutely no movement between the surgical device and lens when the surgical device is gripping the lens while manipulating the lens within the eye. This method would provide the most "positive grip" connection between the surgical device and the intraocular lens during manipulation.

Preferably, the "positive grip" connection between the surgical device and lens is of a type that is releasable upon demand by the surgeon. A preferred embodiment of the apparatus and method according to the present invention utilizes a vacuum cannula, which when a fluid vacuum is applied the cannula a gripping tip of the cannula positively grips a portion of the intraocular lens. The vacuum can be controlled on demand by the surgeon to selectively grip and release upon the surgeon's demand and control. The fluid vacuum can be provided by a hydraulic force or a pneumatic force, and other types may use a combination of both hydraulic and pneumatic forces to "positively grip" at least a portion of the intraocular lens during manipulation of the intraocular lens within the eye.

The preferred embodiment of a fluid vacuum cannula can be configured so that the vacuum cannula can be fit through the same small incision wound as utilized for inserting the intraocular lens through the eye. Specifically, a small incision is made in the eye using a diamond knife or surgical steel knife in the cornea and/or sclera, and then the intraocular lens is inserted through the small incision by an intraocular lens insertion apparatus and/or forceps. After the insertion of the intraocular lens into the eye, a preferred fluid vacuum cannula apparatus according to the present invention is inserted through the same small incision wound to further manipulate the intraocular lens within the eye. It is possible that the lens inserting apparatus can be configured to have a duel function and also be used as the vacuum cannula apparatus according to the present invention. Alternatively, these are separate surgical instruments to be consecutively utilized by the surgeon.

The fluid vacuum source for the fluid vacuum cannula can be a syringe connected to the fluid vacuum. Alternatively, the fluid vacuum source can be a peristaltic pump and/or venturi pump. For example, a phacoemulsification apparatus provided with a peristaltic pump and/or venturi pump can be utilized as a fluid vacuum source. For example, a phacoemulsification apparatus provided with a peristaltic pump and/or venturi pump can be utilized as a fluid vacuum source. Specifically, the fluid vacuum cannula is an attachment configured for connection with the handpiece of the phacoemulsification apparatus.

BRIEF DESCRIPTION OF THE DRAWINGS

FIG. 12 is a left-end view of the syringe shown in FIG. 14.

FIG. 13 is right-end view of the syringe shown in FIG. 14.

FIG. 14 is cross-sectional view of a syringe of the fluid vacuum cannula apparatus according to the present invention.

FIG. 15 is a side view of a plunger tip of the syringe of the fluid vacuum cannula apparatus according to the present invention.

FIG. 16 is a right-end view of the plunger tip shown in FIG. 15.

FIG. 17 is an edge view of a locking washer as shown in FIG. 18.

FIG. 18 is an end view of a locking washer for use with the plunger of the fluid vacuum cannula apparatus according to the present invention.

FIG. 19 is a cross-sectional view of a syringe with a plunger tip according to the present invention.

DETAILED DESCRIPTION OF THE PREFERRED EMBODIMENTS

The apparatus and method according to the present invention can be utilized for manipulating various implants within the eye. The eye can be a human eye or animal eye. For example, the apparatus and method according to the present invention can be used for manipulating an intraocular lens (IOL) such as an anterior chamber intraocular lens, a posterior chamber intraocular lens, a cataract type intraocular lens, a phakic refractive lens (e.g. Implantable Contact Lens™ (ICL™)), a Toric Intraocular Lens™, and other types of IOLs. The apparatus and method according to the present invention can also be used on other type of implants for use in the eye, including capsular rings, sulcus rings, anterior chamber rings, corneal rings (e.g. intra corneal ring), scleral implants, and other eye implants.

The apparatus and method according to the present invention involve "positively gripping" a portion of the lens during manipulation of the lens within the eye. The term "positively gripping" means that there exists little to no movement between the surgical device and the implant when connected together. Preferably, there is absolutely no movement between the surgical instrument and implant when the implant is being manipulated within the eye. Most preferably, the apparatus and method according to the present invention releasably "positively grip" the eye implant to allow the doctor to selectively grip and ungrip the implant upon the surgeon's demand.

Figure 1:
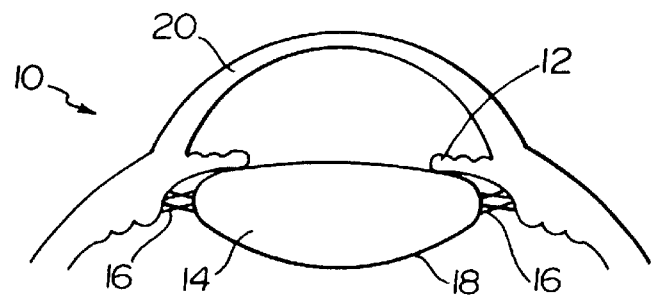
FIG. 1 is a cross-sectional view of an eye indicative of the general structure of the eye.

A human eye 10 is shown in FIG. 1 with the iris 12 in a dilated condition. The iris 12 can be dilated by application of a suitable pharmaceutical for preparing the eye for surgery. The natural crystalline lens 14 is located just beneath the iris 12 and connected by the zonules 16 to the remaining supporting structure of the eye. The natural crystalline lens 14 is enclosed by the capsular bag 18.

Figure 2:
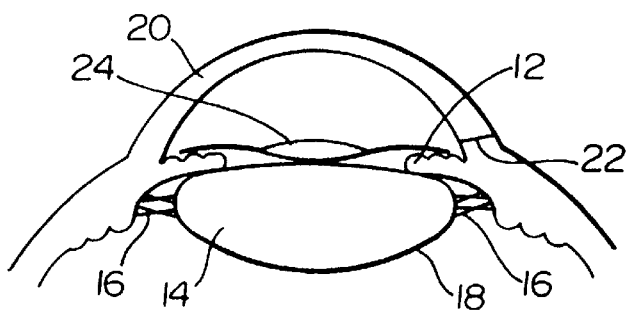
FIG. 2 is a cross-sectional view of the eye indicating a small incision and the placement of a phakic refractive lens initially into the anterior chamber of the eye.

In FIG. 2, a small incision 22 (e.g. approximately 2 mm) is made in the side of the clear cornea 20 with a diamond knife or a surgical steel knife by the surgeon. The phakic refractive lens is inserted through the small incision 22 with a lens insertion apparatus of the type disclosed in U.S. Pat. Nos. 5,499,987, 5,616,148, 5,620,450 and 5,772,666 to Vladimir Feingold, incorporated by reference herein, or by a forceps. Specifically, the phakic refractive lens is preferably a deformable type of IOL which can be folded, rolled or compressed to significantly reduce its outer dimensions so that it can be inserted through the small incision 22. Once inside the eye, the phakic refractive lens 24 unfolds to its normal outer dimensions. In FIG. 2, the phakic refractive lens 24 is in the unfolded condition, however, is shown positioned in front of the dilated iris 12. To complete the procedure, the phakic refractive lens 24 needs to be manipulated by the surgeon to a position between the iris and natural crystalline lens in the posterior chamber of the eye.

Figure 3:
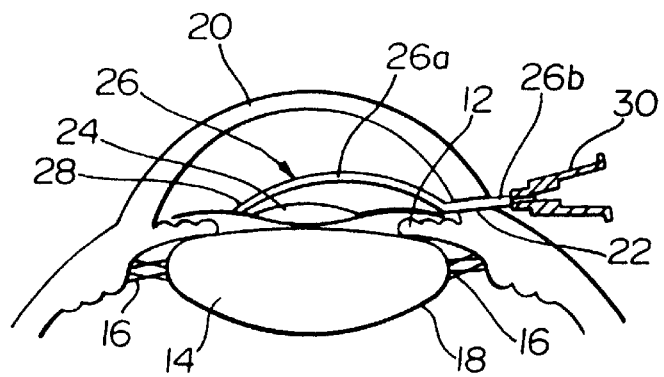
FIG. 3 is a cross-sectional view of the eye showing a vacuum cannula according to the present invention releasably positively engaging with a haptic portion of a phakic refractive lens initially placed in the anterior chamber of the eye.
Figure 4:
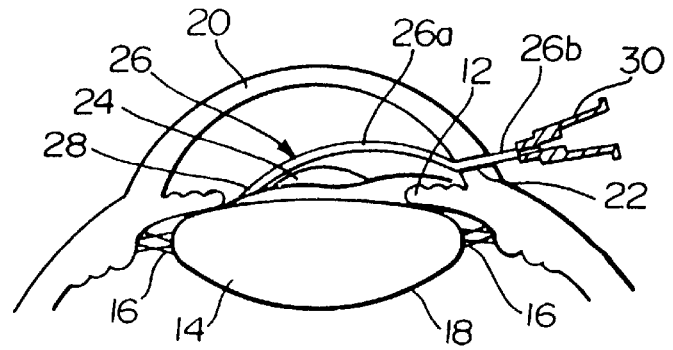
FIG. 4 is a cross-sectional view of the eye with a vacuum cannula extending through the small incision to grip a distal foot pad of the phakic refractive lens to feed the foot pad between the iris and natural crystalline lens of the eye without inadvertent contact of the gripping tip of the vacuum cannula with the natural crystalline lens.
Figure 5:
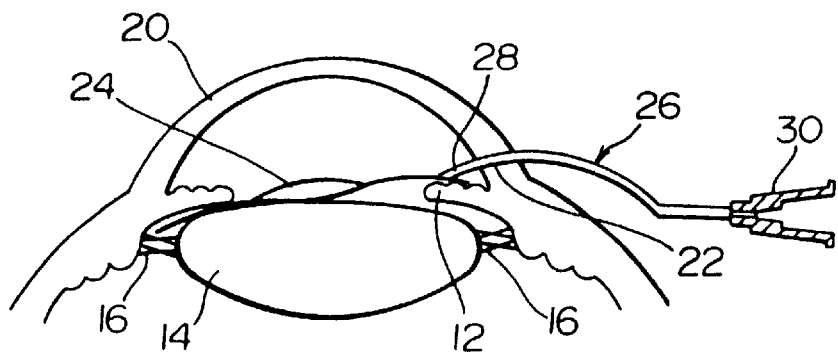
FIG. 5 is a cross-sectional view of the eye with the vacuum cannula of the present invention releasably positively gripping another foot pad at an opposite end of the phakic refractive lens.
Figure 6:
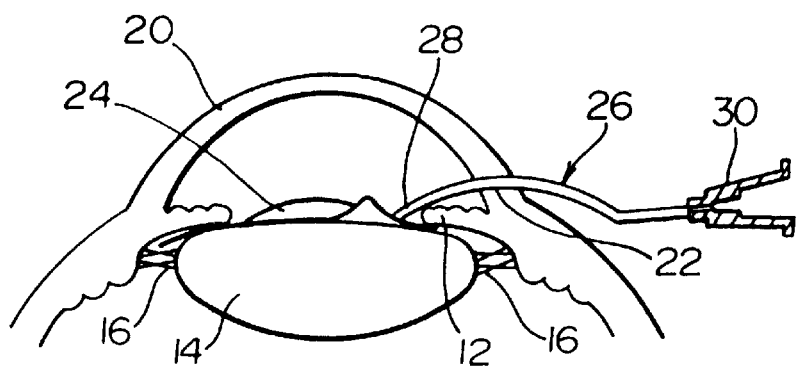
FIG. 6 is a cross-sectional view of the eye with a vacuum cannula according to the present invention gripping a proximal foot pad and bending the foot pad downward to feed the footpad between the iris and natural crystalline lens.
Figure 7:
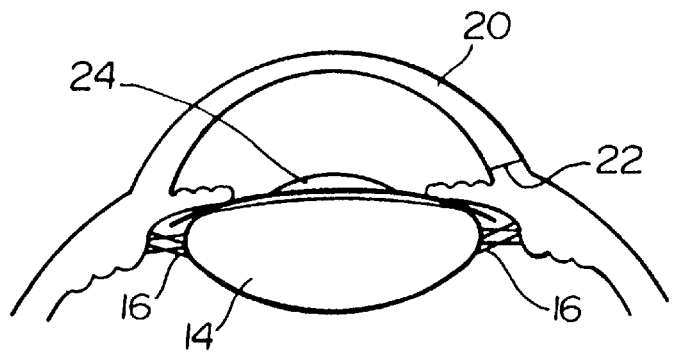
FIG. 7 is a cross-sectional view of the eye with a phakic refractive lens in position between the natural crystalline and the iris and slightly vaulting over a center portion of the natural crystalline lens with the footpads in contact with the zonules of the eye.

The apparatus according to the present invention is utilized for manipulating the intraocular lens within the eye. A preferred embodiment of the apparatus is shown in FIG. 3. Specifically, the apparatus includes a vacuum cannula 26 configured to fit through the small incision 22, shown in FIG. 3. The vacuum cannular is provided with a gripping tip 28 at one end and a vacuum connection 30 (e.g. lure lock connector) at an opposite end. The gripping tip 28 is beveled at an angle to provide proper orientation with a surface of the phakic refractive lens. As shown in FIG. 3, the vacuum cannula 22 is configured with an arc-shaped cannula portion 26a and a straight cannula portion 26b. This configuration allows the phakic refractive lens 26 to be manipulated while minimizing the risk of inadvertent contact with the natural crystalline lens which could potentially cause a surgically induced cataract. Specifically, the arc-shaped cannula portion 26a allows the vacuum cannula 26 to safely vault over the natural crystalline lens 14 to minimize the chance of contact with any portion along the length of the arc-shaped portion 26a. Only the gripping tip 28 comes into close proximity with the natural crystalline lens during manipulation, however, the surgeon's eye is carefully tracking the movement of the gripping tip 28 during the surgical procedure.

Figure 8:
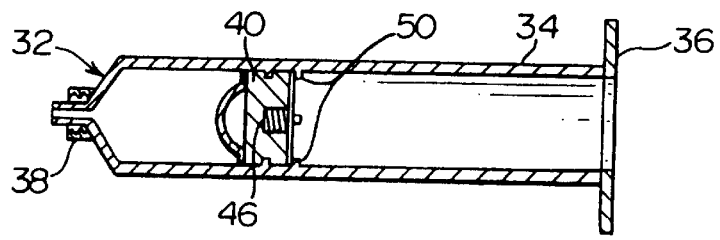
FIG. 8 is a cross-sectional view of a syringe of the fluid vacuum cannula apparatus according to the present invention.
Figure 9:
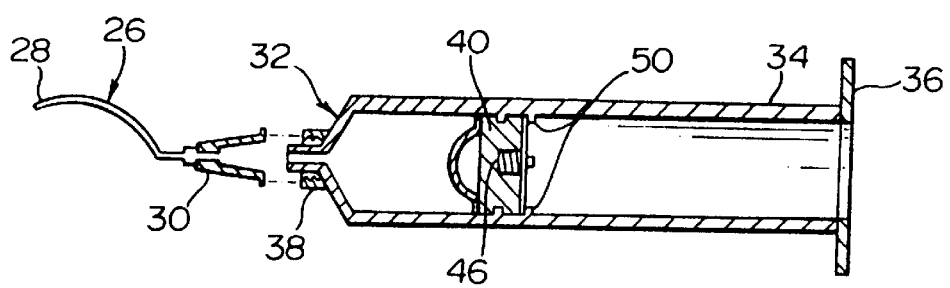
FIG. 9 is a cross-sectional view of the fluid vacuum cannula according to the present invention with the fluid vacuum cannula disconnected from the syringe.

The vacuum cannula apparatus according to the present invention includes the combination of the vacuum cannula 26 and the syringe 32 as shown in FIGS. 8 and 9. The syringe 32 includes a cylindrical-shaped body portion 34 provided with a finger gripping flange 36 at one end and a male type lure lock connector 38 at an opposite end thereof. A slidable plunger tip 40 is provided within the body portion 34.

In a preferred embodiment, the plunger tip 40 is releasably connected to a plunger 42, as shown in FIGS. 8 through 11. For example, the plunger 42 is provided with a threaded male connector 44 cooperating with a threaded female connector 46 of the plunger tip 40. Alternatively, some other suitable mechanical fastener can be utilized for releasably securing the plunger tip 40 to the plunger 42 (e.g. releasable snap fit connection).

A coil spring 48 is provided on the plunger 42 to provide an opposite spring force against the travel of the plunger 42 when the plunger 42 is being forced further into the syringe 32. The spring force provides a certain feedback or feel to the surgeon manipulating the syringe 32, and allows the syringe to automatically withdraw fluid along the vacuum cannula 26 when the force is reduced, for example, when the surgeon releases force exerted by the thumb. Thus, the surgeon does not have to change his or her grip on this syringe 32 when the plunger 42 is allowed to withdraw under the spring force provided by the coil spring 48 (i.e. the thumb remains on the end of the plunger 42 and the forefinger and middle finger remain on opposite edges of the gripping flange 36). In this mode of operation, the surgeon does not need to grip the body portion 34 with one hand while gripping the end of the plunger 42 between the thumb and forefinger with the opposite hand (i.e. allows for one hand operation).

Figure 10:
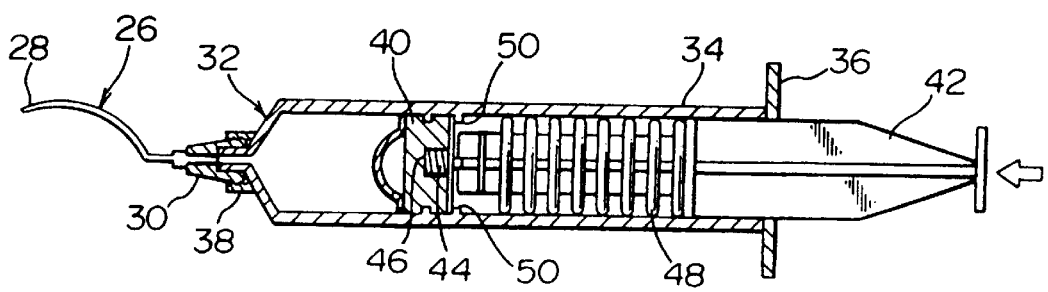
FIG. 10 is a cross-sectional view of the fluid vacuum cannula apparatus according to the present invention with the fluid vacuum cannula connected to the syringe prior to gripping a phakic refractive lens.
Figure 11:
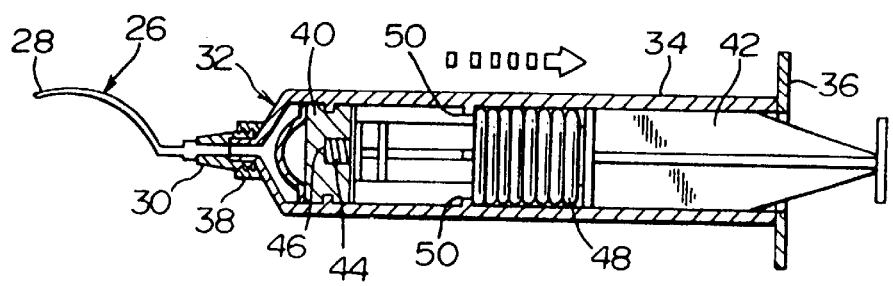
FIG. 11 is a cross-sectional view of the fluid vacuum cannula apparatus according to the present invention in a position readied for providing gripping of a portion of phakic refractive lens.

An inner wall of the body portion 34 is provided with protrusions 50, as shown in FIG. 14, for cooperating with the plunger tip 40 as shown in FIG. 10 and the spring 48, as shown in FIG. 11. Specifically, the protrusions 50 provide a stop to limit the egress of the plunger head 40, as shown in Figure 10, and provide a stop for the spring 48 to exert a reverse spring force on the plunger 42, as shown in FIG. 11.

As shown in FIG. 19, the plunger tip 40 is provided with a locking washer 40a having four indents 40b, as shown in FIG. 18. The four indents 40b are equally spaced at 90° increments around the periphery of the locking washing 40a and match up with the four protrusions 50 equally spaced within the inner wall of the body portion 34 of the syringe 32. When the indents 40b of the locking washer 40a are aligned with the four protrusions 50 of the body portion 34, the plunger tip 40 can be moved past the protrusions 50. The plunger 42 is then rotated so that the indents 40b of the locking washer 40a no longer align with the four protrusions 50, which now act as stops, which prevents the plunger 42 from being withdrawn from the syringe 32.

Figure 20:
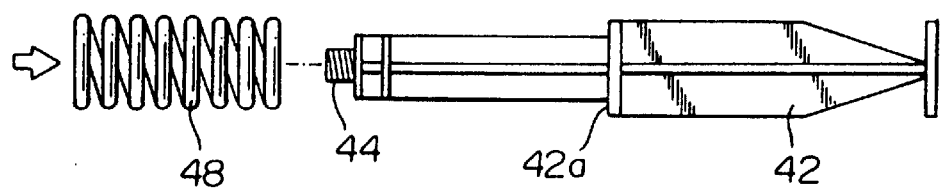
FIG. 20 is a side view of a coil spring disassembled from the plunger of the syringe of the fluid vacuum cannula apparatus according to the present invention.
Figure 21:
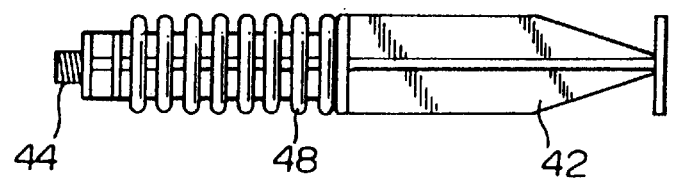
FIG. 21 is a side view of a coil spring assembled on the plunger of the syringe of the fluid vacuum cannula apparatus according to the present invention.

The plunger 42 is provided with the spring 48, as shown in FIGS. 20 and 21. The spring 48 cooperates with an end flange 42a, as shown in FIG. 21, and shown in operation in FIG. 11.

The method according to the present invention includes the step of positively gripping a portion of an implant (e.g. IOL, phakic refractive lens, etc.) with a surgical instrument within the eye. Preferably, the method includes the step of releasably positively gripping a portion of the implant for manipulating the implant within the eye. More preferably, the method involves positively gripping and releasing a portion of the implant when manipulating the implant within the eye at least one time and possibly multiple times to finally position the implant into place within the eye. The preferred method utilizes a releasable positive grip provided by hydraulic and/or pneumatic force. For example, a vacuum cannula is provided having a gripping tip that can releasably grip a portion of the implant when manipulating the implant within the eye. The vacuum cannula is preferably configured to grip the implant at different portions of the implant to perform various manipulations on the implant. For example, the vacuum cannula is configured to grip haptic edge portions (e.g. foot pads) of a phakic refractive lens to work the edge portions under the dilated iris for ultimate placement of the phakic refractive lens between the natural crystalline lens and the rear surface of the iris.

A more preferred method according to the present invention is the step of positively gripping a portion of a phakic refractive lens in a manner to prevent contact of the apparatus with the natural crystalline lens of the eye to prevent an inadvertent surgically induced cataract. A preferred embodiment utilizes a vacuum cannula having a gripping tip that can grip anterior surface portions of a phakic refractive lens including a haptic portion and/or lens portion to position the phakic refractive lens within the eye. The vacuum cannula is preferably configured so that the phakic refractive lens can be releasably gripped by the vacuum cannula on one side (i.e. anterior side) of the phakic refractive lens using the lens itself to protect inadvertent contact of the gripping tip of the vacuum cannula with the surface of the natural crystalline lens to prevent inadvertent surgically induced cataract.

The vacuum cannula embodiment according to the present invention is very preferred in operation, since the vacuum cannula tends to pull the phakic refractive lens slightly away from the natural crystalline lens when vacuum is applied from the gripping tip of the vacuum cannula to an anterior surface portion of the phakic refractive lens. This operation further prevents the inadvertent contact of the gripping tip of the vacuum cannula from contact with the natural crystalline lens, since the vacuum force of the vacuum cannula pulls the phakic refractive lens towards the gripping tip of the vacuum cannula and slightly away from the natural crystalline lens in close proximity thereto. In this manner, the surgeon can on demand releasably grip an anterior surface portion of the phakic refractive lens without any potential of contact of the gripping end of the vacuum cannula with the surface of the natural crystalline lens. On demand, the surgeon can grip and release a multiple number of times and/or at a multiple number of different locations on the anterior surface of the phakic refractive lens to perform various manipulating techniques. In this manner, each of the four corner located foot pads of the plate-type haptic of the Implantable Contact Lens can be gripped and slightly bend to feed each foot between the iris and natural crystalline lens of the eye without contact of the gripping end of the vacuum cannula with the natural crystalline lens.

Figure 22:
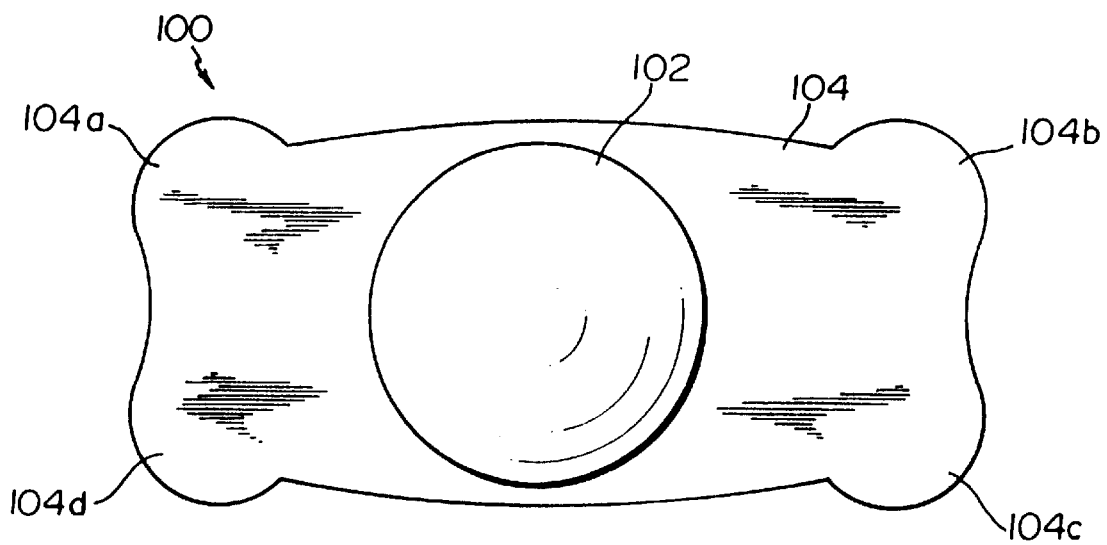
FIG. 22 is a top planar view of a phakic refractive lens to be manipulated by the apparatus and method according to the present invention.

A phakic refractive lens 100 for use with the present invention is shown in FIG. 22. The phakic refractive lens 100 includes lens portion 102 and haptic portion 104. The haptic portion 104 is provided with four (4) foot pads 104a–d at the four (4) corners of the phakic refractive lens.

What is claimed is:

1. A fluid vacuum cannula apparatus for releasably positively gripping a portion of an implant for the eye, comprising:

a vacuum cannula having a gripping tip configured for releasably positively gripping a portion of the eye implant; and a fluid vacuum source connected to the vacuum cannula for providing a fluid vacuum to the gripping tip of the vacuum cannula configured for releasably positively gripping a portion of the eye implant, said fluid vacuum source being a syringe provided with a spring loaded plunger, said plunger being provided with a plunger tip having a locking washer with at least one indent and an inner wall of said syringe being provided with at least one protrusion to cooperate with the indent of the locking washer to allow the plunger to be rotated to lock said plunger within said syringe.

2. The apparatus according to claim 1, wherein the vacuum cannula is provided with an arc-shaped portion having said gripping tip at one end, and a straight cannula portion connected to an opposite end of the arc-shaped cannula portion.

3. The apparatus according to claim 1, wherein the vacuum cannula and said syringe are provided with a lure lock connection to releasably connect the fluid vacuum cannula to the syringe.

4. The apparatus according to claim 1, wherein the gripping tip is defined by a bevel tip portion of the vacuum cannula.

5. The apparatus according to claim 1, wherein a spring of said spring-loaded plunger engages with the at least one protrusion provided on the inner surface of said syringe to provide a stop for said spring.

6. The apparatus according to claim 1, wherein said plunger is provided with a flange portion for cooperating with an end of a coil spring of the spring-loaded plunger.

7. The apparatus according to claim 1, wherein said vacuum source is a peristaltic pump.

8. The apparatus according to claim 1, wherein said vacuum source is a venturi pump.

9. The apparatus according to claim 1, wherein said vacuum source is a peristaltic pump and a venturi pump.

10. The apparatus according to claim 1, wherein said vacuum source is provided by a phacoemulsification apparatus.

* * * * *